(12) United States Patent
Yoshiara et al.

(10) Patent No.: US 11,690,597 B2
(45) Date of Patent: Jul. 4, 2023

(54) ULTRASONIC DIAGNOSTIC APPARATUS

(71) Applicant: CANON MEDICAL SYSTEMS CORPORATION, Otawara (JP)

(72) Inventors: Hiroki Yoshiara, Utsunomiya (JP); Tomohisa Imamura, Nasushiobara (JP); Akihiro Kakee, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 554 days.

(21) Appl. No.: 16/802,324

(22) Filed: Feb. 26, 2020

(65) Prior Publication Data

US 2020/0268350 A1 Aug. 27, 2020

(30) Foreign Application Priority Data

Feb. 27, 2019 (JP) .................................. 2019-033906

(51) Int. Cl.
*A61B 8/00* (2006.01)
*A61B 8/08* (2006.01)
(Continued)

(52) U.S. Cl.
CPC ............ *A61B 8/469* (2013.01); *A61B 8/5207* (2013.01); *G01S 15/8977* (2013.01);
(Continued)

(58) Field of Classification Search
CPC .................. G06T 7/0012; G06T 5/007–10
See application file for complete search history.

(56) References Cited

U.S. PATENT DOCUMENTS 6,704,438 B1 * 3/2004 Alexandru ................ G06T 5/10
382/128
2006/0058677 A1 * 3/2006 Okada .................. G01S 15/8954
600/459
(Continued)

FOREIGN PATENT DOCUMENTS

JP 7-250833 A 10/1995
JP 2007-97938 A 4/2007
WO WO 2012/063930 A1 5/2012

OTHER PUBLICATIONS

Kirkhorn (Introduction to IQ-demodulation of RF-data; Sep. 15, 1999).*

(Continued)

*Primary Examiner* — Carolyn A Pehlke
(74) *Attorney, Agent, or Firm* — Oblon, McClelland, Maier & Neustadt, L.L.P.

(57) ABSTRACT

The ultrasonic diagnostic apparatus according to the present embodiment includes a frequency characteristic analysis circuit, a filter setting circuit, and a filter processing circuit. The frequency characteristic analysis circuit performs a frequency analysis on a first reception signal corresponding to a region of interest of each depth, and acquires a frequency characteristic of each depth. The filter setting circuit sets a reception filter of each depth based on the acquired frequency characteristic of each depth such that the acquired frequency characteristic of each depth shows a predetermined frequency characteristic. The filter processing circuit applies the set reception filter of each depth to a second reception signal corresponding to the region of interest of each depth, the second reception signal being after the first reception signal, and converts the second reception signal into a third reception signal corresponding to the region of interest of each depth.

17 Claims, 12 Drawing Sheets

(51) Int. Cl.
*G06T 7/00* (2017.01)
*G01S 15/89* (2006.01)

(52) U.S. Cl.
CPC .. *G06T 7/0012* (2013.01); *G06T 2207/10132* (2013.01); *G06T 2207/30004* (2013.01)

(56) References Cited

U.S. PATENT DOCUMENTS

| | | | |
|---|---|---|---|
| 2013/0096429 A1 | 4/2013 | Noguchi | |
| 2016/0331352 A1* | 11/2016 | Kawashima | A61B 8/5269 |
| 2018/0116631 A1* | 5/2018 | Taniguchi | A61B 8/14 |
| 2021/0077078 A1* | 3/2021 | Hu | A61B 8/5246 |

OTHER PUBLICATIONS

Katja's homepage on sinusoids, complex numbers and modulation (www.katjaas.nl/FFToutput/FFToutput.html; Jun. 27, 2010).*
Japanese Office Action dated Nov. 15, 2022, issued in Japanese Patent Application No. 2019-033906, 4 pages.

* cited by examiner

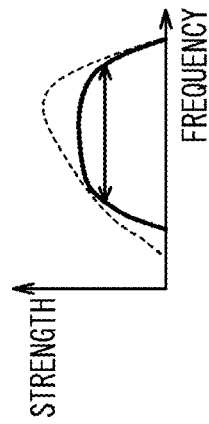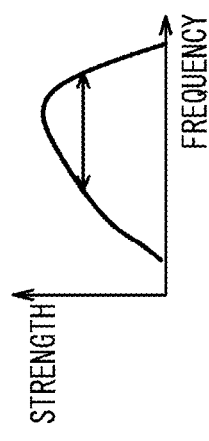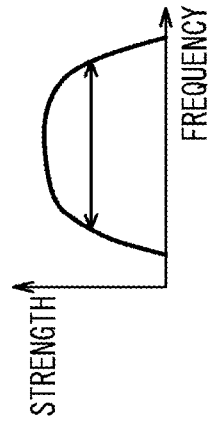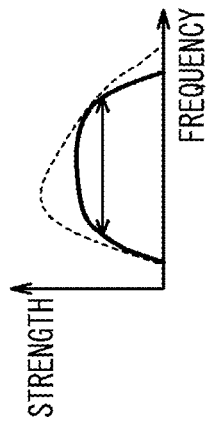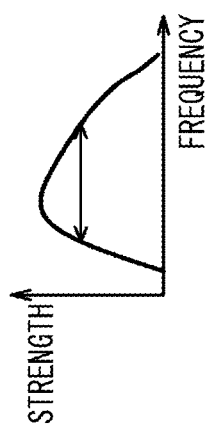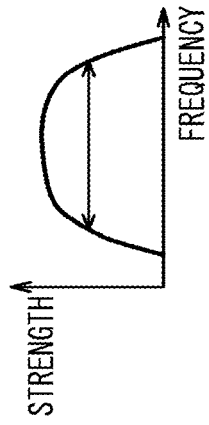
FIG. 2A
FIG. 2B

ULTRASONIC DIAGNOSTIC APPARATUS

CROSS-REFERENCE TO RELATED APPLICATION

This application is based upon and claims the benefit of priority from Japanese Patent Application No. 2019-033906, filed on Feb. 27, 2019, the entire contents of which are incorporated herein by reference.

FIELD

An embodiment as an aspect of the present invention relates to an ultrasonic diagnostic apparatus.

BACKGROUND

In the medical field, an ultrasonic diagnostic apparatus is used for imaging the inside of a subject using ultrasonic waves generated by multiple transducers (piezoelectric vibrators) of an ultrasonic probe. The ultrasonic diagnostic apparatus causes the ultrasonic probe, which is connected to the ultrasonic diagnostic apparatus, to transmit ultrasonic waves into the subject, generates a reception signal based on a reflected wave, and acquires a desired ultrasonic image by image processing.

There are some methods of generating an ultrasonic image in the ultrasonic diagnostic apparatus. In the first method, a radio frequency (RF) signal, which is a reception signal, is delayed and added, a quadrature detection (de-modulation) is performed, and a conversion to an I/Q signal composed of an "I (In-phase)" signal and a "Q (Quadrature-phase)" signal is performed. In the second method, a quadrature detection of an RF signal is performed, an I/Q signal is converted to baseband, and a delay addition is performed. The former method is also called "RF beamforming". The latter method is also called "I/Q beamforming". Functions for improving the image quality of an ultrasonic image in the I/Q beamforming include a function of controlling a gain of an amplifier, a function of controlling a reception delay curve of a delay control circuit, etc.

Each of FIGS. 2A and 2B is a conceptual diagram for explaining a target frequency characteristic having the substantially flat bandwidth close to a designed frequency characteristic in the ultrasonic diagnostic apparatus according to the present embodiment.

Each of FIGS. 3A to 3E is a conceptual diagram for explaining a method of setting a reception filter in the ultrasonic diagnostic apparatus according to the present embodiment.

Figure 4:
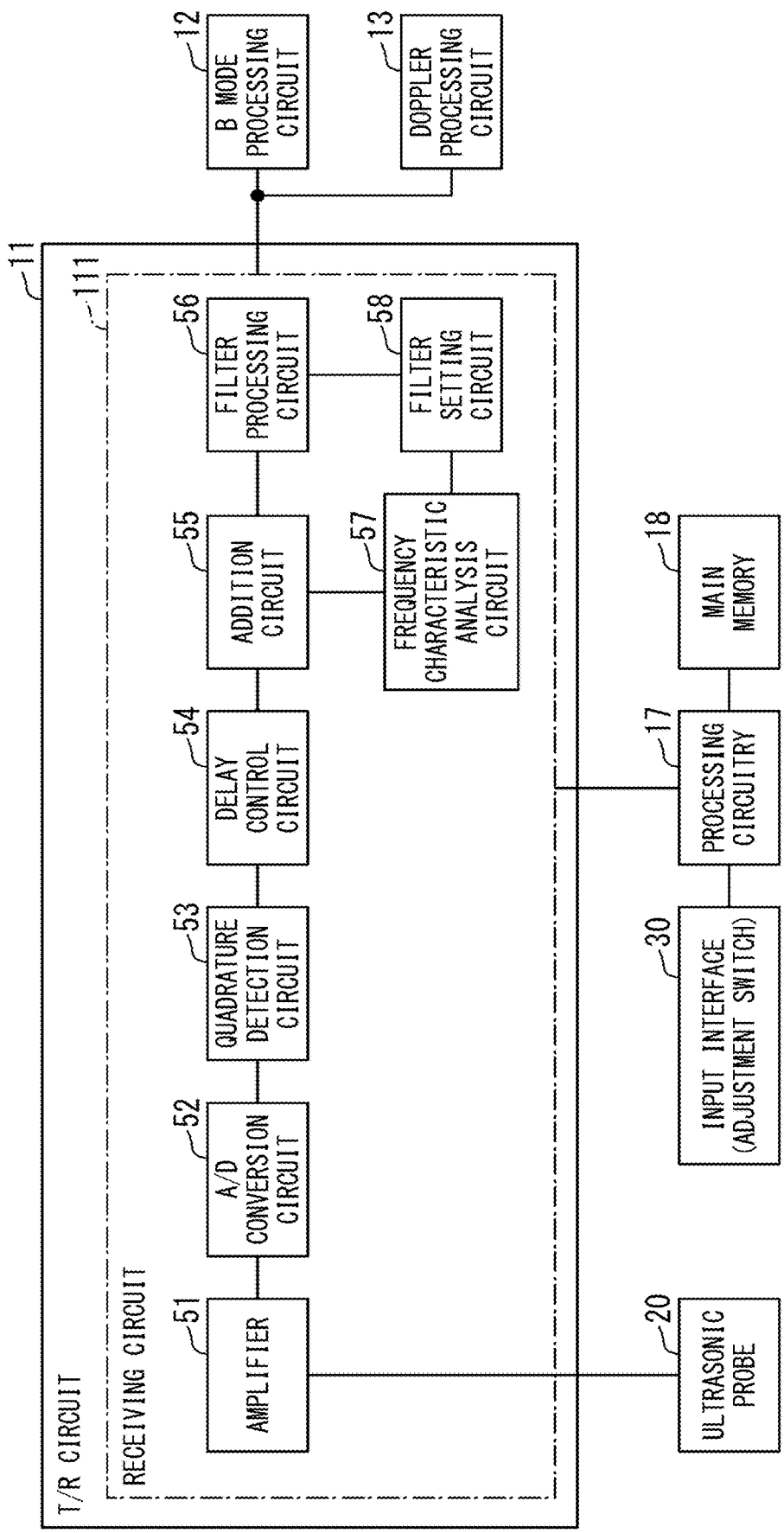

FIG. 4 is a block diagram showing a configuration of a receiving circuit provided in a transmitting/receiving circuit in the ultrasonic diagnostic apparatus according to the present embodiment.

Figure 5:
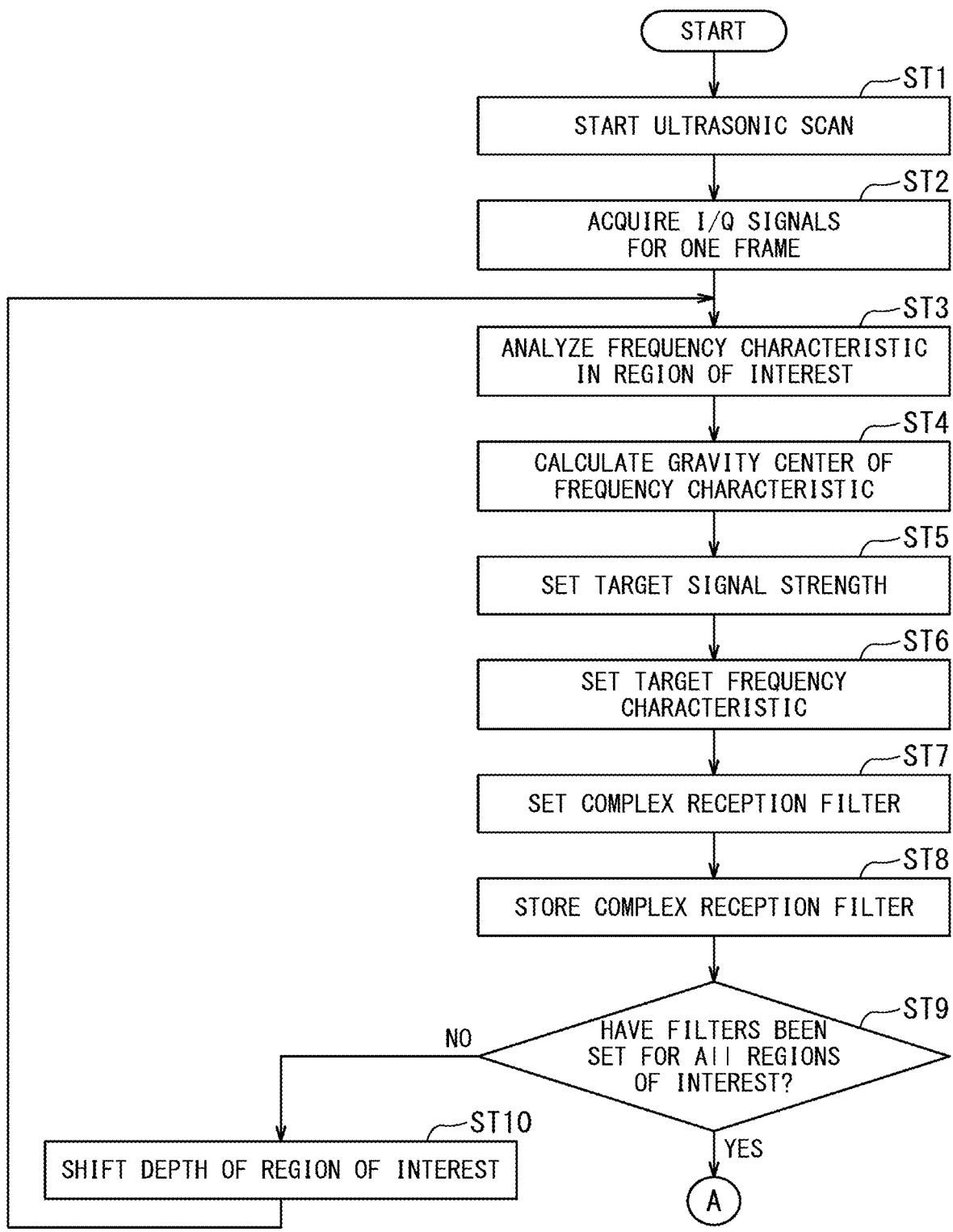

FIG. 5 is a diagram showing an operation of the ultrasonic diagnostic apparatus according to the present embodiment as a flowchart.

Figure 6:
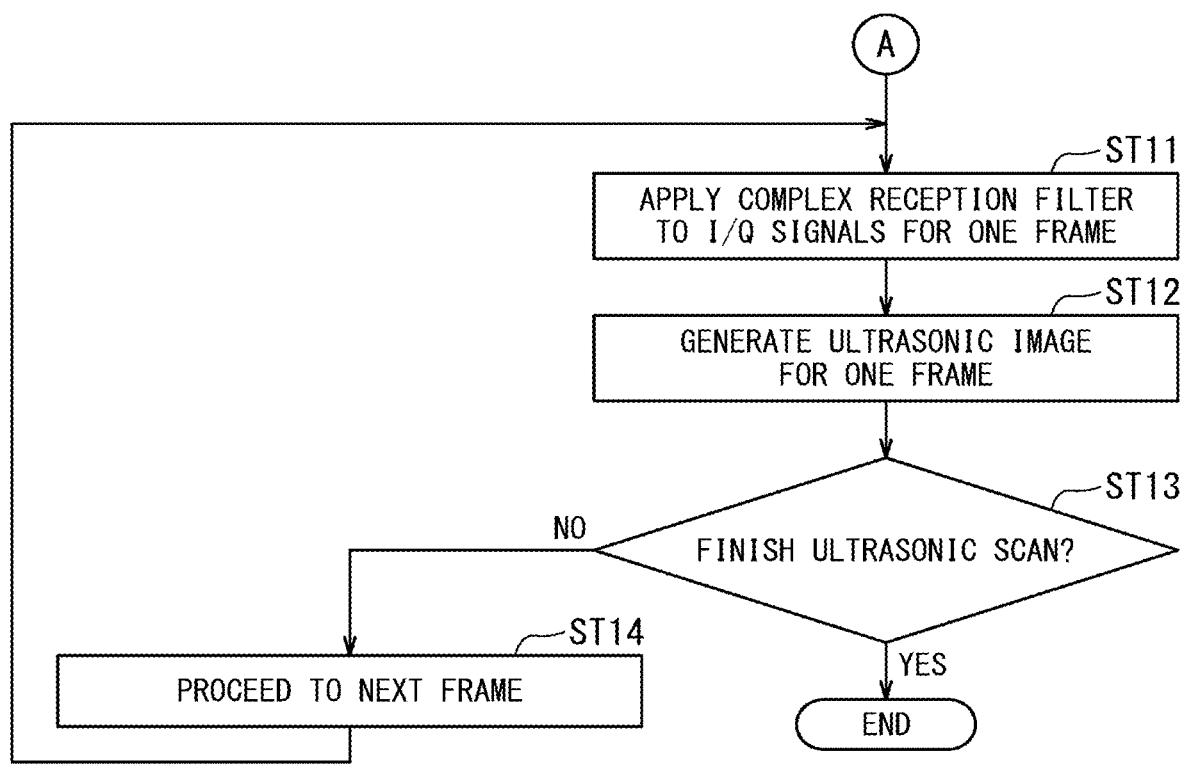

FIG. 6 is a diagram showing an operation of the ultrasonic diagnostic apparatus according to the present embodiment as a flowchart.

Figure 7A:
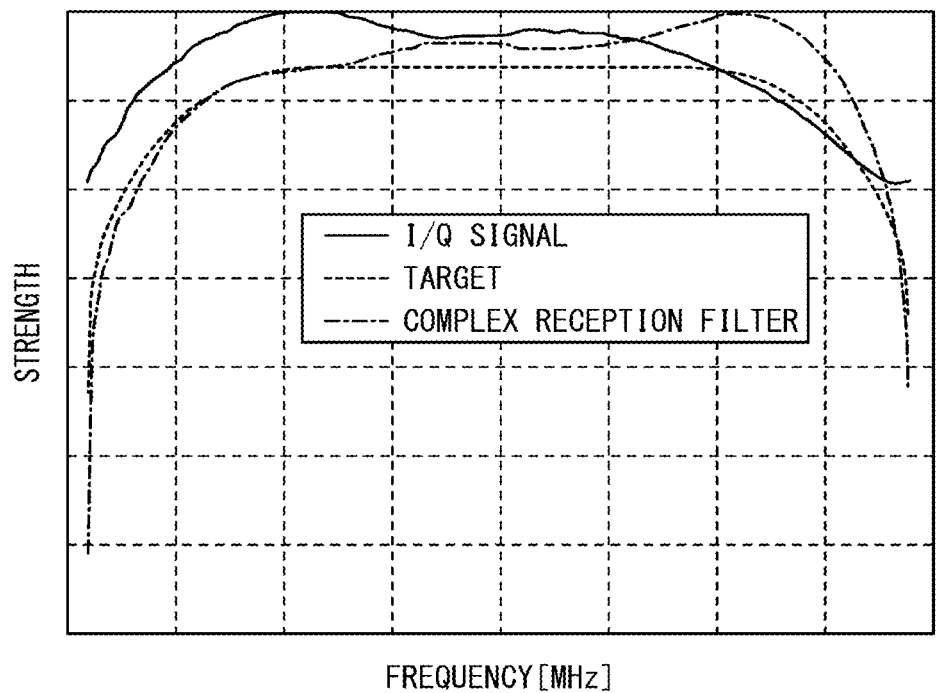
Figure 7B:
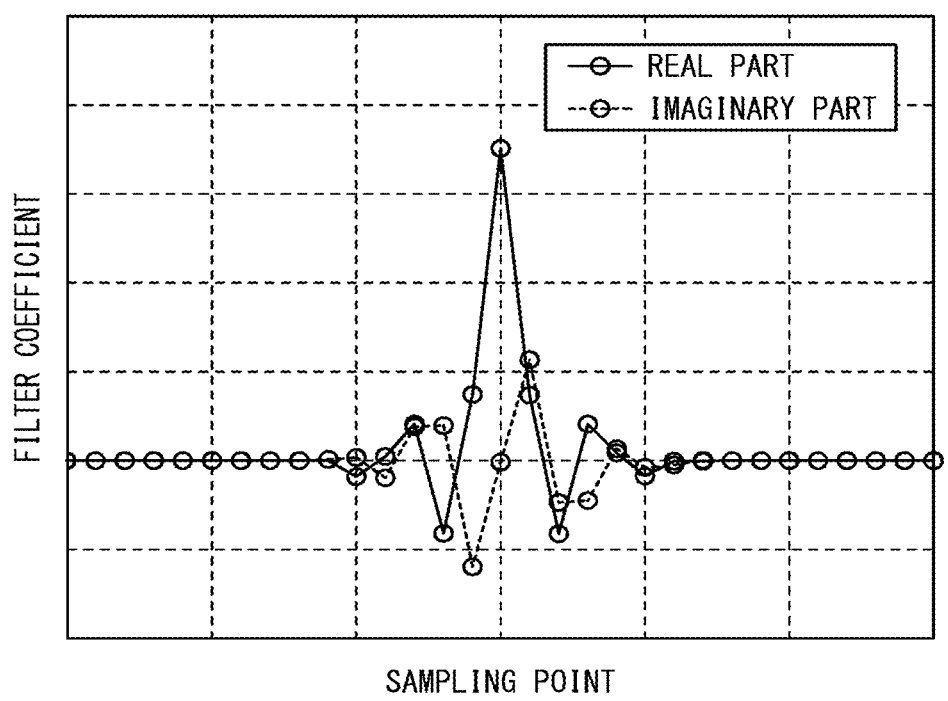

Each of FIGS. 7A and 7B is a diagram showing a complex reception filter of the region of interest in the ultrasonic diagnostic apparatus according to the present embodiment.

Figure 8A:
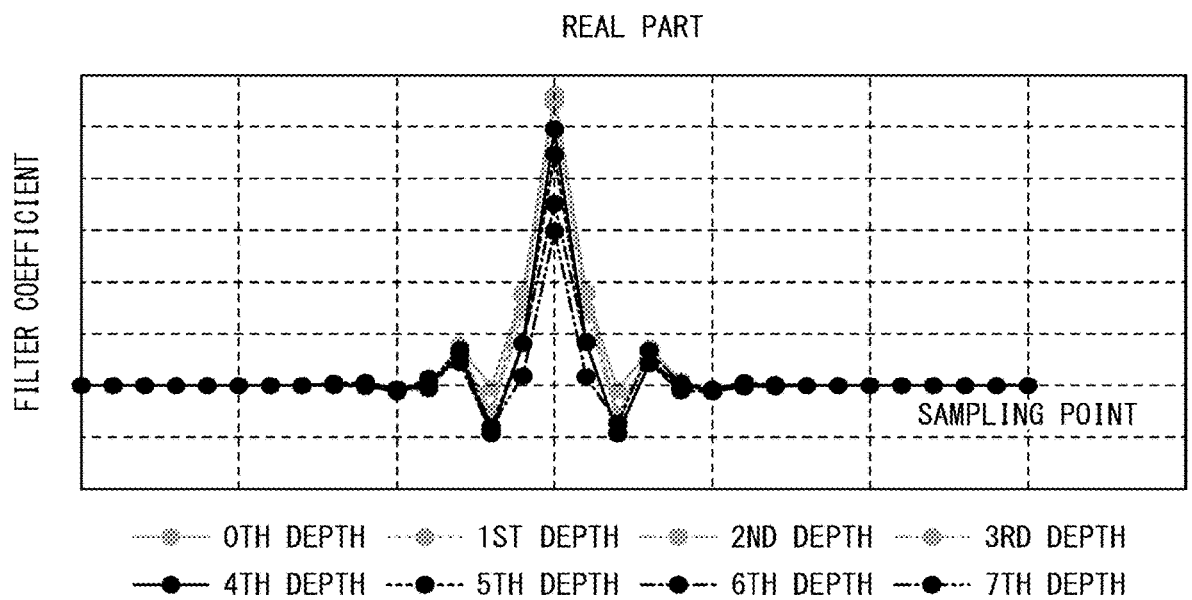
Figure 8B:
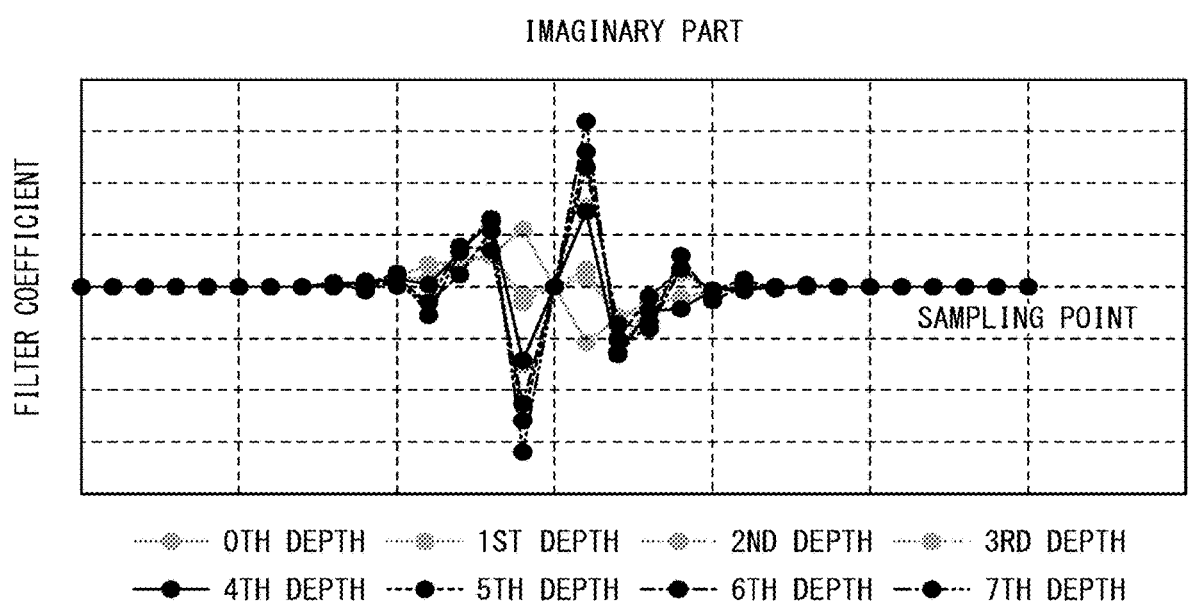

Each of FIGS. 8A and 8B is a diagram showing a complex reception filter of each region of interest in the ultrasonic diagnostic apparatus according to the present embodiment.

Figure 9:
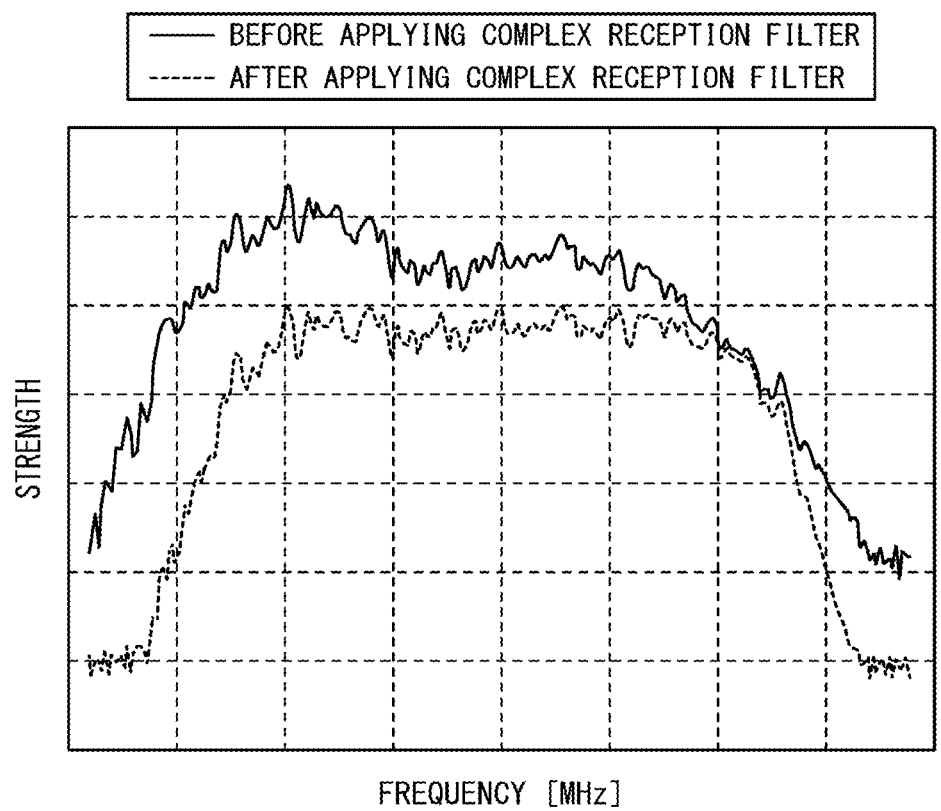

FIG. 9 is a diagram showing, as a frequency characteristic, an effect acquired when a complex reception filter is applied to an I/Q signal in a predetermined region of interest in the ultrasonic diagnostic apparatus according to the present embodiment.

Figure 10A:
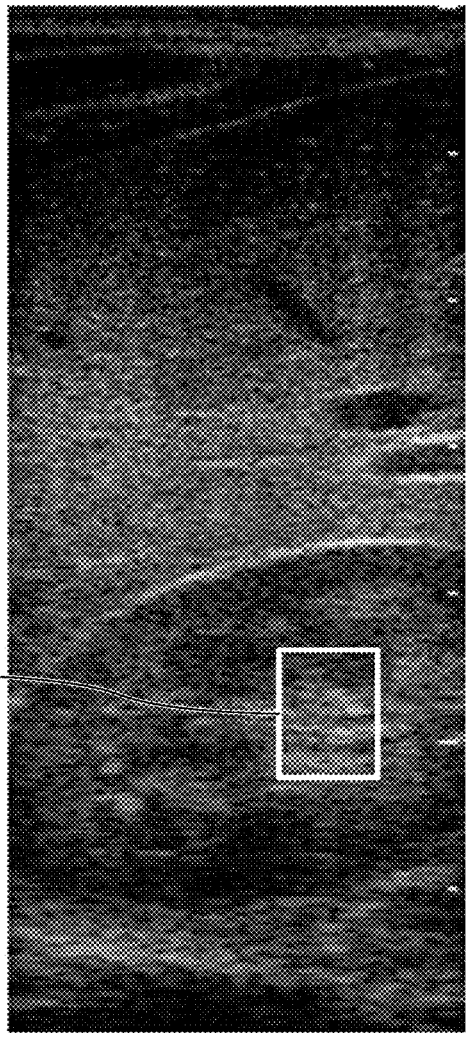
Figure 10B:
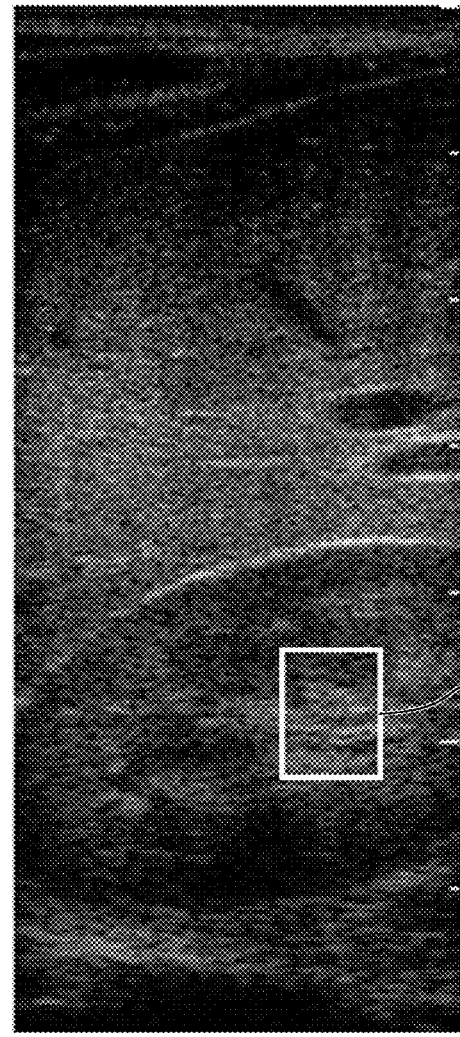

Each of FIGS. 10A and 10B is a diagram showing an effect acquired when a complex reception filter is applied to an I/Q signal in a predetermined region of interest as an ultrasonic image in the ultrasonic diagnostic apparatus according to the present embodiment.

Figure 11:
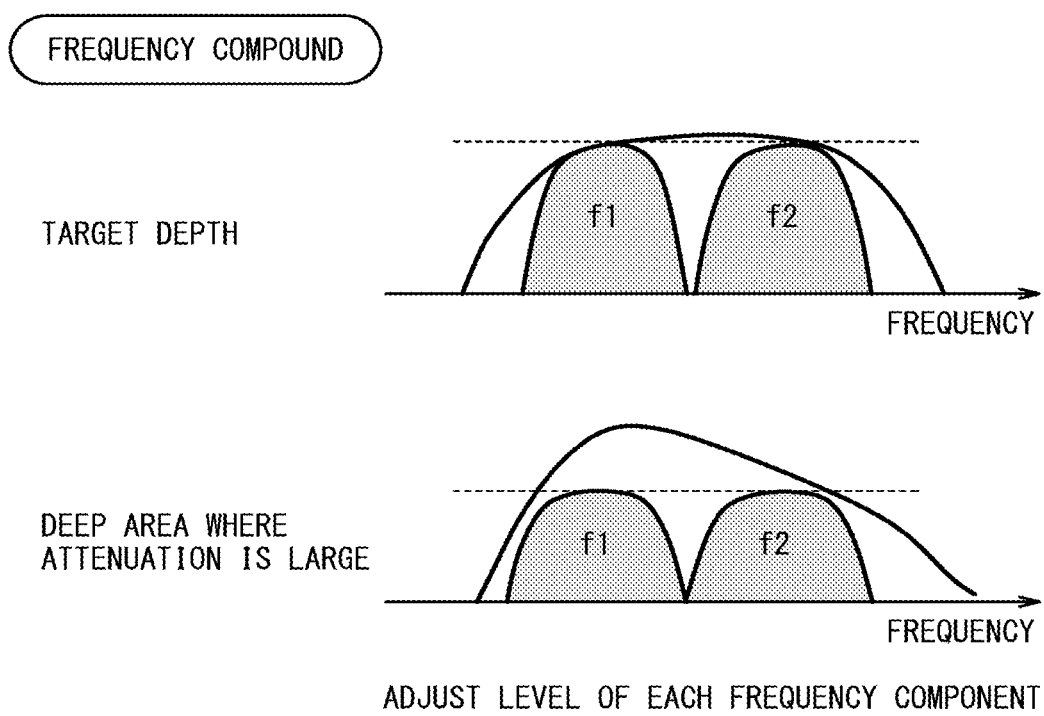

FIG. 11 is a diagram for explaining a frequency compound in the ultrasonic diagnostic apparatus according to the present embodiment.

Figure 12:
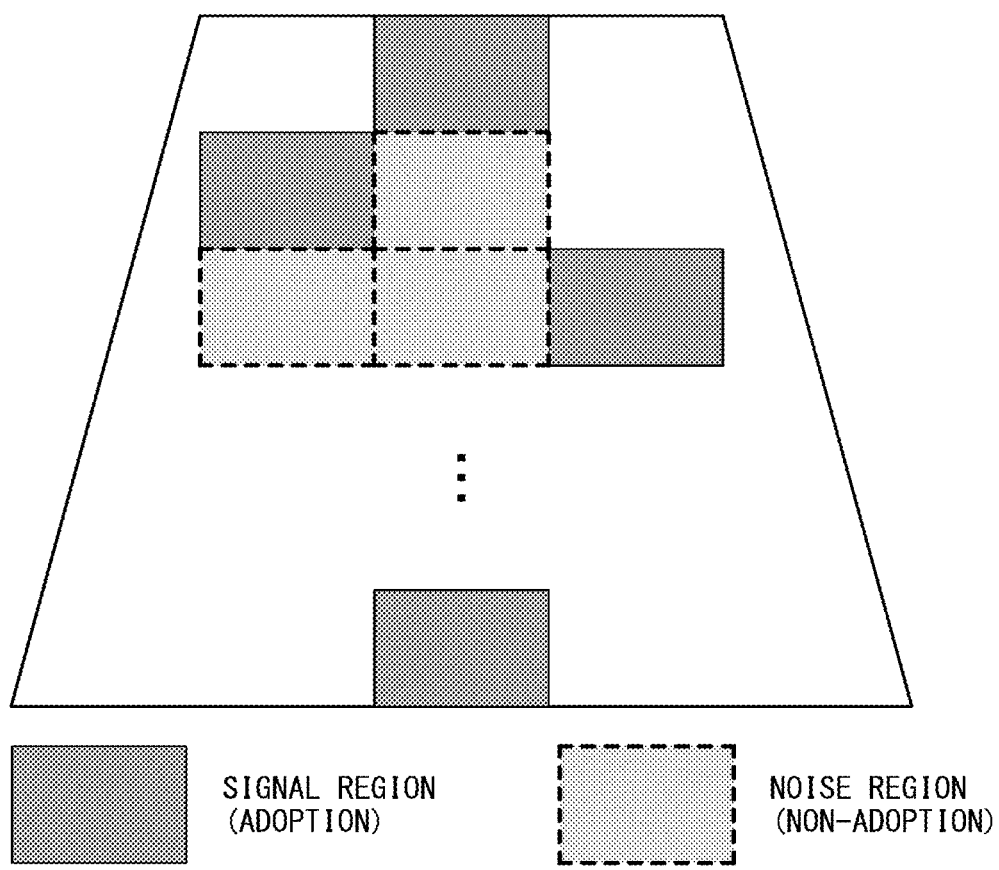

FIG. 12 is a diagram showing a method of selecting a predetermined region of interest from set multiple regions of interest of the same depth in the ultrasonic diagnostic apparatus according to the present embodiment.

DETAILED DESCRIPTION

An ultrasonic diagnostic apparatus according to a present embodiment will be described with reference to the accompanying drawings.

The ultrasonic diagnostic apparatus according to the present embodiment includes a frequency characteristic analysis circuit, a filter setting circuit, a filter processing circuit, and an image generating circuit. The frequency characteristic analysis circuit performs a frequency analysis on a first reception signal corresponding to a region of interest of each depth among reception signals of ultrasonic waves, and acquires a frequency characteristic of each depth. The filter setting circuit sets a reception filter of each depth based on the acquired frequency characteristic of each depth such that the acquired frequency characteristic of each depth shows a predetermined frequency characteristic. The filter processing circuit applies the set reception filter of each depth to a second reception signal corresponding to the region of interest of each depth among the reception signals, the second reception signal being after the first reception signal, and converts the second reception signal into a third reception signal corresponding to the region of interest of each depth among the reception signals. The image generating circuit generates an ultrasonic image in substantially real time based on the converted third reception signal corresponding to the regions of interest.

1. Ultrasonic Diagnostic Apparatus

Figure 1:
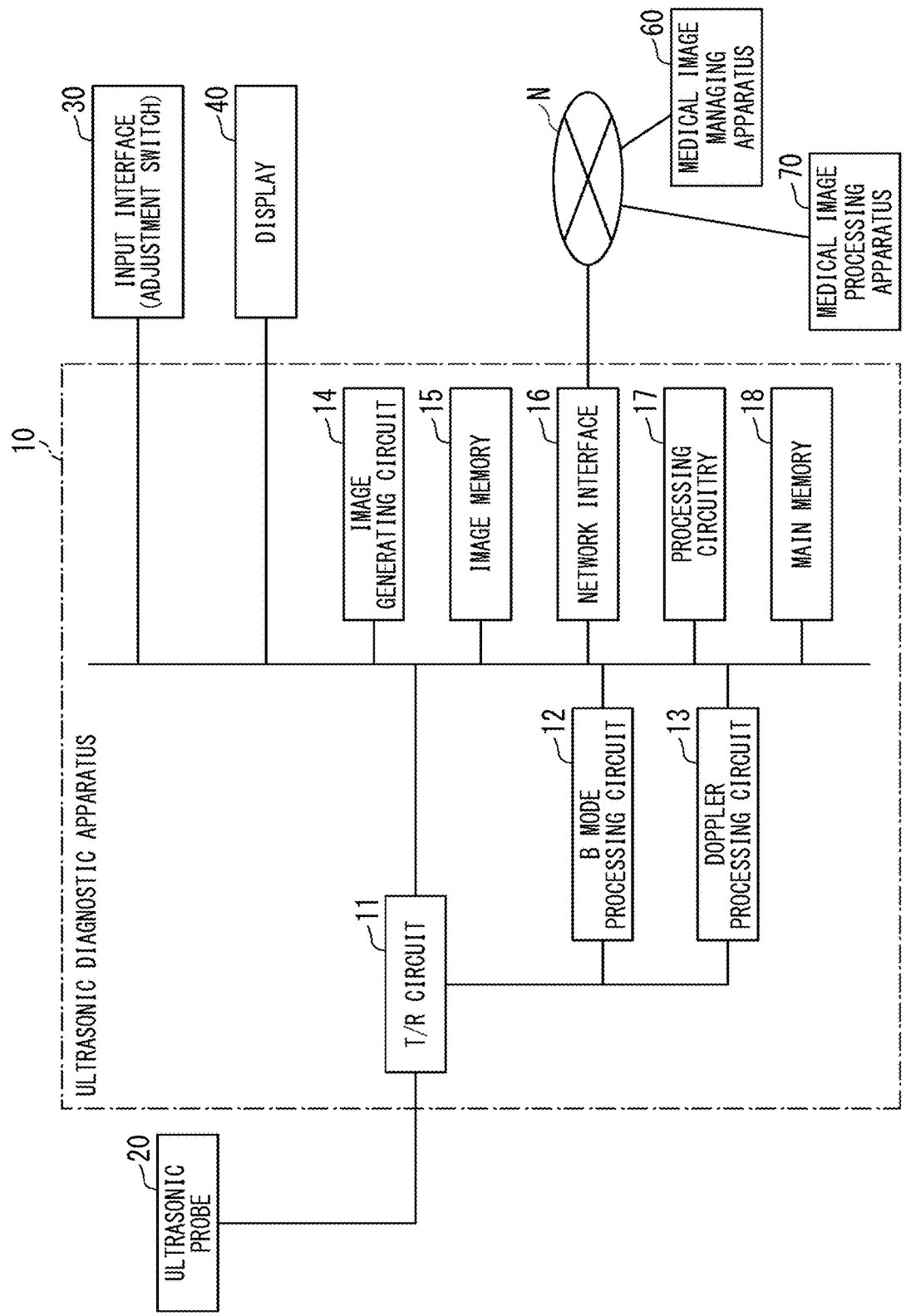
FIG. 1 is a schematic diagram showing a configuration of an ultrasonic diagnostic apparatus according to a present embodiment.

FIG. 1 is a schematic diagram showing a configuration of an ultrasonic diagnostic apparatus according to a present embodiment.

FIG. 1 shows an ultrasonic diagnostic apparatus 10 according to a present embodiment. FIG. 1 shows an ultrasonic probe 20, an input interface 30, and a display 40. Note that an apparatus in which at least one of the ultrasonic probe 20, the input interface 30 and the display 40 are added to the ultrasonic diagnostic apparatus 10 may be referred to as "ultrasonic diagnostic apparatus". In the following description, a case will be described in which the ultrasonic probe 20, the input interface 30 and the display 40 are all provided outside "ultrasonic diagnostic apparatus".

The ultrasonic diagnostic apparatus 10 includes a transmitting/receiving (T/R) circuit 11, a B mode processing circuit 12, a Doppler processing circuit 13, an image generating circuit 14, an image memory 15, a network interface 16, processing circuitry 17, and a main memory 18. The circuits 11 to 14 are configured by application-specific integrated circuits (ASICs) and the like. However, the present invention is not limited to this case, and all or part of the functions of the circuits 11 to 14 may be realized by the processing circuitry 17 executing a program.

Further, all or part of the members 11 to 18 may be provided in the ultrasonic probe 20.

The T/R circuit 11 has a transmitting circuit and a receiving circuit (not shown). Under the control of the processing circuitry 17, the T/R circuit 11 controls transmission directivity and reception directivity in transmission and reception of ultrasonic waves. The case where the T/R circuit 11 is provided in the ultrasonic diagnostic apparatus 10 will be described, but the T/R circuit 11 may be provided in the ultrasonic probe 20, or may be provided in both of the ultrasonic diagnostic apparatus 10 and the ultrasonic probe 20. The T/R circuit 11 is one example of a transmitter-and-receiver.

The transmitting circuit has a pulse generating circuit, a transmission delay circuit, a pulsar circuit and the like, and supplies a drive signal to ultrasonic transducers. The pulse generating circuit repeatedly generates rate pulses for forming transmission ultrasonic waves at a predetermined rate frequency. The transmission delay circuit converges the ultrasonic waves generated from the ultrasonic transducer of the ultrasonic probe 20 into a beam shape, and gives a delay time of each piezoelectric transducer necessary for determining the transmission directivity to each rate pulse generated by the pulse generating circuit. In addition, the pulsar circuit applies drive pulses to each ultrasonic transducer at a timing based on the rate pulses. The transmission delay circuit arbitrarily adjusts the transmission direction of the ultrasonic beam transmitted from a piezoelectric transducer surface by changing the delay time given to each rate pulse.

The receiving circuit receives reception signals received by the ultrasonic transducer, performs various processing on the reception signals, and generates echo data. The configuration of the receiving circuit will be described later with reference to FIG. 4.

Under the control of the processing circuitry 17, the B mode processing circuit 12 receives the echo data from the receiving circuit, performs logarithmic amplification, envelope detection processing and the like, thereby generate data (2D or 3D data) which signal intensity is represented by brightness of luminance. This data is an example of the raw data, and is generally called "B mode data". The B mode processing circuit 12 is one example of a B mode processer.

The B mode processing circuit 12 may change the frequency band to be visualized by changing the detection frequency using filtering processing. By using the filtering processing function of the B mode processing circuit 12, harmonic imaging such as the contrast harmonic imaging (CHI) or the tissue harmonic imaging (THI) is performed.

That is, the B mode processing circuit 12 may separate the reflected waves from within a subject into which the contrast agent is injected into harmonic data (or sub-frequency data) and fundamental wave data. The harmonic data (or sub-frequency data) corresponds to reflected waves with a harmonic component whose reflection source is the contrast agent (microbubbles or bubbles) in the subject. The fundamental wave data corresponds to reflected waves with a fundamental wave component whose reflection source is tissue in the subject. The B mode processing circuit 12 generates B mode data for generating contrast image data based on the reflected wave data (reception signals) of the harmonic component, and generates B mode data for generating fundamental wave image data based on the reflected wave data (reception signals) with the fundamental wave component.

In the THI by using the filtering processing function of the B mode processing circuit 12, it is possible to separate harmonic data or sub-frequency data which is reflected wave data (reception signals) of a harmonic component from reflected wave data of the subject. Then, the B mode processing circuit 12 generates B mode data for generating tissue image data in which the noise component is removed from the reflected wave data (reception signals) of the harmonic component.

When the CHI or THI harmonic imaging is performed, the B mode processing circuit 12 may extract the harmonic component by a method different from the method using the above-described filtering. With respect to harmonic imaging, an imaging method called the amplitude modulation (AM) method, the phase modulation (PM) method or the AM-PM method in which the AM method and the PM method are combined is performed. With the AM method, the PM method, and the AM-PM method, ultrasonic transmission with different amplitudes and phases is performed multiple times on the same scanning line.

Thereby, the T/R circuit 11 generates and outputs multiple reflected wave data (reception signals) in each scanning line. The B mode processing circuit 12 extracts harmonic components by performing addition/subtraction processing according to the modulation method on the multiple reflected wave data (reception signals) of each scanning line. The B mode processing circuit 12 performs envelope detection processing etc. on the reflected wave data (reception signals) of the harmonic component to generate B mode data.

For example, when the PM method is performed, the T/R circuit 11 controls the ultrasonic waves having the same amplitude and reversed-phase polarities, for example (−1, 1), to be transmitted twice by each scanning line under a scan sequence set by the processing circuitry 17. The T/R circuit 11 generates a reception signal based on transmission of "−1" and a reception signal based on transmission of "1". The B mode processing circuit 12 adds these two reception signals. As a result, the fundamental wave component is removed, and a signal in which the second harmonic component mainly remains is generated. Then, the B mode processing circuit 12 performs envelope detection processing and the like on such a signal to generate B mode data using THI or CHI.

Alternatively, for example, in the THI, an imaging method using the second harmonic component and a difference tone component included in the reception signals has been put to practical use. With the imaging method using the difference tone component, transmission ultrasonic waves are transmitted from the ultrasonic probe 20, and the transmission ultrasonic waves have, for example, a composite waveform in which a first fundamental waves with a center frequency "f1" and a second fundamental waves with a center frequency "f2" larger than the center frequency "f1" are combined. Such a composite waveform is a waveform in which a waveform with the first fundamental waves and a waveform with the second fundamental waves which phases being adjusted with each other are combined, such that the difference tone component having the same polarity as the second harmonic component is generated. The T/R circuit 11 transmits the transmission ultrasonic waves of the composite waveform, for example, twice while inverting the phase. In such a case, for example, the B mode processing circuit 12 removes the fundamental wave component by adding two reception signals, and performs an envelope detection process etc. after extracting a harmonic component in which the difference tone component and the second harmonic component are mainly left.

Under the control of the processing circuitry 17, the Doppler processing circuit 13 frequency-analyzes the phase information from the echo data from the receiving circuit, thereby generating data (2D or 2D data) acquired by extracting moving data of moving subject such as average speed, dispersion, power and the like for multiple points. This data is an example of the raw data, and is generally called "Doppler data". In the present embodiment, the moving subject is, for example, blood flow, tissue such as heart wall, or contrast agent. The Doppler processing circuit 13 is one example of a Doppler processer.

Under the control of the processing circuitry 17, the image generating circuit 14 generates an ultrasonic image presented in a predetermined luminance range as image data based on the reception signals received by the ultrasonic probe 20. For example, the image generating circuit 14 generates, as an ultrasonic image, a B mode image in which the intensity of the reflected wave is represented by luminance from the two-dimensional B mode data generated by the B mode processing circuit 12. In addition, the image generating circuit 14 generates a color Doppler image from the two-dimensional Doppler data generated by the Doppler processing circuit 13. The color Doppler image includes an average speed image representing moving state information, a dispersion image, a power image, or a combination image thereof. The image generating circuit 14 is an example of an image generating unit.

In the present embodiment, the image generating circuit 14 generally converts (scan-converts) a scanning line signal sequence of ultrasonic scanning into a scanning line signal sequence of a video format used by a television or the like, and generates ultrasonic image data for display. Specifically, the image generating circuit 14 generates ultrasonic image data for display by performing coordinate conversion according to the ultrasonic scanning mode of the ultrasonic probe 20. The image generating circuit 14 performs various image processes other than the scan conversion. For example, the image generating circuit 14 performs image processing (smoothing processing) for regenerating an average luminance image using multiple image frames after scan conversion, image processing using a differential filter in the image (processing for enhancing edges) and the like. Further, the image generating circuit 14 combines character information of various parameters, scales, body marks, and the like with the ultrasonic image data.

That is, the B mode data and the Doppler data are the ultrasonic image data before the scan conversion processing. The data generated by the image generating circuit 14 is ultrasonic image data for display after the scan conversion processing. The B-mode data and the Doppler data are also called raw data. The image generating circuit 14 generates two-dimensional ultrasonic image data for display from the two-dimensional ultrasonic image data before the scan conversion processing.

Further, the image generating circuit 14 performs coordinate conversion on the three-dimensional B mode data generated by the B mode processing circuit 12, thereby generates three-dimensional B mode image data. The image generating circuit 14 performs coordinate conversion on the three-dimensional Doppler data generated by the Doppler processing circuit 13, thereby generates three-dimensional Doppler image data. The image generating circuit 14 generates "three-dimensional B mode image data or three-dimensional Doppler image data" as "three-dimensional ultrasonic image data (volume data)".

Further, the image generating circuit 14 performs a rendering processing on the volume data to generate various two-dimensional image data for displaying the volume data on the display 40. The image generating circuit 14 performs a processing of generating a multi planer reconstruction (MPR) image data from the volume data by performing, for example, an MPR processing that is one of the rendering processing. Further, the image generating circuit 14 performs, for example, volume rendering (VR) processing for generating two-dimensional image data reflecting three-dimensional data that is one of the rendering processing.

The image memory 15 includes multiple memory cells in one frame in two axial directions, and includes a two-dimensional memory which is a memory provided with multiple frames. The two-dimensional memory as the image memory 15 stores one frame or an ultrasonic image of the multiple frames generated by the image generating circuit 14 as two-dimensional image data under the control of the processing circuitry 17. The image memory 15 is an example of a storage.

Under the control of the processing circuitry 17, the image generating circuit 14, if necessary, performs three-dimensional reconstruction for performing an interpolation processing on the ultrasonic images arranged in the two-dimensional memory as the image memory 15, thereby generates an ultrasonic image as volume data in the three-dimensional memory as the image memory 15. A known technique is used as the interpolation processing.

The image memory 15 may include a three-dimensional memory which is a memory having multiple memory cells in three axis directions (X-axis, Y-axis, and Z-axis directions). The three-dimensional memory as the image memory 15 stores the ultrasonic image generated by the image generating circuit 14 as volume data under the control of the processing circuitry 17.

The network interface 16 implements various information communication protocols according to the network form. The network interface 16 connects the ultrasonic diagnostic apparatus 10 and other devices such as the external medical image managing apparatus 60 and the medical image processing apparatus 70 according to these various protocols. An electrical connection or the like via an electronic network is applied to this connection. In the present embodiment, the electronic network means an entire information communication network using telecommunications technology. The electronic network includes a wired/wireless hospital backbone local area network (LAN) and the Internet network, as well as a telephone communication line network, an optical fiber communication network, a cable communication network, a satellite communication network, or the like.

Further, the network interface 16 may implement various protocols for non-contact wireless communication. In this case, the ultrasonic diagnostic apparatus 10 can directly transmit/receive data to/from the ultrasonic probe 20, for example, without going through the network. The network interface 16 is one example of a network connector.

The processing circuitry 17 may mean a processor such as a dedicated or general-purpose CPU (central processing unit), an MPU (microprocessor unit), a GPU (Graphics Processing Unit), or the like. The processing circuitry 17 may mean an ASIC, a programmable logic device, or the like. The programmable logic device is, for example, a simple programmable logic device (SPLD), a complex programmable logic device (CPLD), and a field programmable gate array (FPGA).

Further, the processing circuitry 17 may be constituted by a single circuit or a combination of independent circuit elements. In the latter case, the main memory 18 may be provided individually for each circuit element, or a single main memory 18 may store programs corresponding to the functions of the circuit elements. The processing circuitry 17 is one example of a processor.

The main memory 18 is constituted by a semiconductor memory element such as a random-access memory (RAM), a flash memory, a hard disk, an optical disk, or the like. The main memory 18 may be constituted by a portable medium such as a universal serial bus (USB) memory and a digital video disk (DVD). The main memory 18 stores various processing programs (including an operating system (OS) and the like besides the application program) used in the processing circuitry 17 and data necessary for executing the programs. In addition, the OS may include a graphical user interface (GUI) which allows the operator to frequently use graphics to display information on the display 40 to the operator and can perform basic operations by the input interface 30. The main memory 18 is one example of a storage.

The ultrasonic probe 20 includes microscopic transducers (piezoelectric elements) on the front surface portion, and transmits and receives ultrasonic waves to a region including a scan target, for example, a region including a lumen. Each transducer is an electroacoustic transducer, and has a function of converting electric pulses into ultrasonic pulses at the time of transmission and converting reflected waves to electric signals (reception signals) at the time of reception. The ultrasonic probe 20 is configured to be small and lightweight, and is connected to the ultrasonic diagnostic apparatus 10 via a cable (or wireless communication).

The ultrasonic probe 20 is classified into types such as a linear type, a convex type, a sector type, etc. depending on differences in scanning system. Further, the ultrasonic probe 20 is classified into a 1D array probe in which transducers are arrayed in a one-dimensional (1D) manner in the azimuth direction, and a 2D array probe in which transducers are arrayed in a two-dimensional (2D) manner in the azimuth direction and in the elevation direction, depending on the array arrangement dimension. The 1D array probe includes a probe in which a small number of transducers are arranged in the elevation direction.

In the present embodiment, when a three-dimensional (3D) scan, that is, a volume scan is executed, the 2D array probe having a scan type such as the linear type, the convex type, the sector type, or the like is used as the ultrasonic probe 20. Alternatively, when the volume scan is executed, the 1D probe having a scan type such as the linear type, the convex type, the sector type and the like and having a mechanism that mechanically oscillates in the elevation direction is used as the ultrasonic probe 20. The latter probe is also called a mechanical 4D probe.

The input interface 30 includes an input device operable by an operator, and a circuit for inputting a signal from the input device. The input device may be a trackball, a switch, a mouse, a keyboard, a touch pad for performing an input operation by touching an operation surface, a touch screen in which a display screen and a touch pad are integrated, a non-contact input circuit using an optical sensor, an audio input circuit, and the like. When the input device is operated by the operator, the input interface 30 generates an input signal corresponding to the operation and outputs it to the processing circuitry 17.

The input interface 30 may further include an adjustment switch for adjusting a frequency characteristic of a reception filter to be described later. The input interface 30 is one example of an input unit.

The display 40 is constituted by a general display output device such as a liquid crystal display or an organic light emitting diode (OLED) display. The display 40 displays various kinds of information under the control of the processing circuitry 17. The display 40 is one example of a display unit.

FIG. 1 shows the medical image managing apparatus 60 and the medical image processing apparatus 70 which are external devices of the ultrasonic diagnostic apparatus 10. The medical image managing apparatus 60 is, for example, a digital imaging and communications in medicine (DICOM) server, and is connected to a device such as the ultrasonic diagnostic apparatus 10 such that data can be transmitted and received via the network N. The medical image managing apparatus 60 manages a medical image such as an ultrasonic image generated by the ultrasonic diagnostic apparatus 10 as a DICOM file.

The medical image processing apparatus 70 is connected to devices such as the ultrasonic diagnostic apparatus 10 and the medical image managing apparatus 60 such that data is transmitted and received via the network N. An Example of the medical image processing apparatus 70 includes a workstation that performs various image processing on the ultrasonic image generated by the ultrasonic diagnostic apparatus 10 and a portable information processing terminal such as a tablet terminal. It should be noted that the medical image processing apparatus 70 is an offline apparatus and may be an apparatus capable of reading an ultrasonic image generated by the ultrasonic diagnostic apparatus 10 via a portable storage medium.

Subsequently, the concept of the configuration and function of the receiving circuit provided in the T/R circuit 11 will be described with reference to FIGS. 2 and 3.

The receiving circuit provided in the T/R circuit 11 has a frequency characteristic analysis circuit (for example, "frequency characteristic analysis circuit 57" shown in FIG. 4), a filter setting circuit (for example, "filter setting circuit 58" shown in FIG. 4), and a filter processing circuit (for example, "filter processing circuit 56" shown in FIG. 4). The frequency characteristic analysis circuit perform a frequency analysis on a reception signal of a predetermined depth based on the reception signals of the ultrasonic wave from the ultrasonic probe 20, and acquires the frequency characteristic. The filter setting circuit sets a reception filter that corrects the frequency characteristic at a predetermined depth such that the frequency characteristic at a predetermined depth acquired by the frequency characteristic analysis circuit shows the predetermined frequency characteristic. The filter processing circuit applies the reception filter set by the filter setting circuit to the reception signal of a predetermined depth such that feedback is performed.

For example, the frequency characteristic analysis circuit perform the frequency-analysis on a reception signal in each region of interest according to the depth and acquires a frequency characteristic in each region of interest. The filter setting circuit sets a reception filter that corrects the frequency characteristic of each region of interest in each region of interest such that the frequency characteristic of each region of interest acquired by the frequency characteristic analysis circuit shows a predetermined frequency characteristic. The filter processing circuit applies the reception filter in each region of interest set by the filter setting circuit to the reception signal in each region of interest such that feedback is performed.

That is, the filter setting circuit sets a reception filter that is variable according to the depth and that corrects the reception signal so as to exhibit a frequency characteristic having a substantially flat bandwidth over a wide range. It should be noted that "substantially flat" means that the absolute value of the slope of the tangent line formed by each point on the waveform is equal to or smaller than a threshold value, that is, it is rather level. In addition, the reception filter may correct the reception signal so as to exhibit symmetrical (for example, Gaussian function) frequency characteristics on the low frequency side and the high frequency side with respect to the center frequency.

FIG. 2 is a conceptual diagram for explaining a target frequency characteristic having the substantially flat bandwidth close to a designed frequency characteristic.

The left side of each of FIGS. 2A and 2B shows a designed frequency characteristic. The center of each of FIGS. 2A and 2B shows a frequency characteristic based on a reception signal in the region of interest in the clinic practice. The right side of each of FIGS. 2A and 2B shows a target frequency characteristic having a frequency characteristic of a substantially flat bandwidth close to a substantially flat bandwidth in design. FIG. 2A shows a frequency characteristic particularly in a shallow part when ultrasonic attenuation is small and high frequency is dominant in the clinical practice. FIG. 2B shows a frequency characteristic particularly in a deep part when ultrasonic attenuation is large and low frequency is dominant in clinical practice.

The filter setting circuit calculates a target frequency characteristic shown on the right side based on a designed frequency characteristic shown on the left side of FIG. 2A and a clinical frequency characteristic shown at the center. For example, the target frequency characteristic has a characteristic that becomes substantially flat in a wide band.

As shown on the right side of FIG. 2A, the target frequency characteristic has a wide band on the high frequency side, and the intensity is not biased between the high frequency side and the low frequency side. The reception filter set by the filter setting circuit shapes the waveform of the clinical frequency characteristic such that the clinical frequency characteristic shown at the center of FIG. 2A is close to a substantially flat bandwidth shown on the left side.

On the other hand, the filter setting circuit calculates a target frequency characteristic shown on the right side based on a designed frequency characteristic shown on the left side of FIG. 2B and a clinical frequency characteristic shown at the center. For example, the target frequency characteristic has a characteristic that becomes substantially flat in a wide band.

As shown on the right side of FIG. 2B, the target frequency characteristic has a wide band on the low frequency side, and the intensity is not biased between the high frequency side and the low frequency side. The reception filter set by the filter setting circuit shapes the waveform of the clinical frequency characteristic such that the clinical frequency characteristic shown at the center of FIG. 2B is close to a substantially flat bandwidth shown on the left side.

Each of FIGS. 3A to 3E is a conceptual diagram for explaining a method of setting a reception filter.

Figure 3A:
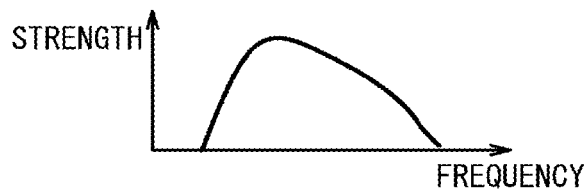
Figure 3B:
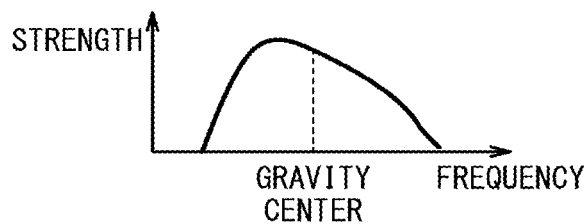
Figure 3C:
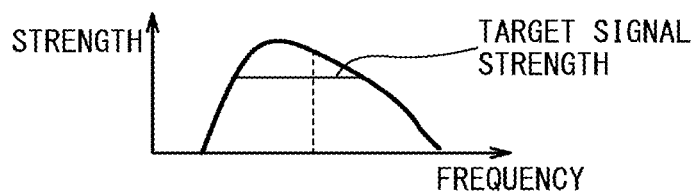

FIG. 3A shows frequency characteristics acquired by frequency-analyzing a reception signal in a region of interest corresponding to the depth among reception signals of one frame. FIG. 3A has the same waveform as shown at the center of FIG. 2B. FIG. 3B shows the gravity center calculated based on the frequency characteristics shown in FIG. 3A in a broken line. FIG. 3C shows a substantially flat bandwidth of the target set by the gravity center and the target signal strength shown in FIG. 3B.

Figure 3D:
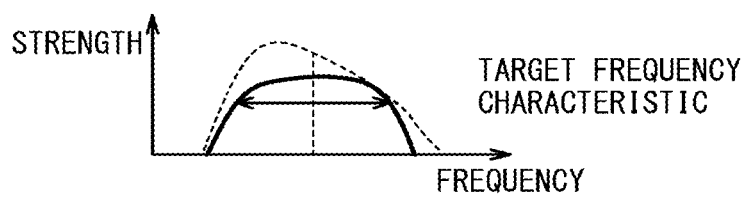
Figure 3E:
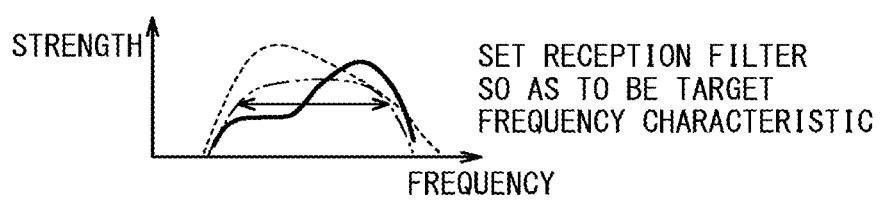

FIG. 3D shows, in a thick solid line, a frequency characteristic having the signal strength shown in FIG. 3C and having a substantially flat bandwidth close to the target substantially flat bandwidth. FIG. 3E shows, in a thick solid line, in which the frequency characteristic of FIG. 3A is set to indicate the target frequency characteristic of FIG. 3D.

As shown in FIGS. 3A to 3E, the filter setting circuit sets a reception filter, thereby brings the substantially flat bandwidth indicated by the frequency characteristic of the reception signal in each region of interest in the clinical practice closer to the substantially flat bandwidth indicated by the designed frequency characteristic.

The reception signals for acquiring the frequency characteristics may be RF signals or I/Q signals. That is, the beam forming method may be RF beam forming or I/Q beam forming. With the RF beamforming method, the RF signals are delayed and added, subjected to quadrature detection (demodulation), converted into I/Q signals each including an "I (In-phase)" signal and a "Q (Quadrature-phase)" signal, and an ultrasonic image is generated. With the I/Q beamforming method, the RF signals are subjected to quadrature detection, converted to an I/Q basebands, delayed and added, and an ultrasonic image is generated. Hereinafter, a case where the reception signals for acquiring frequency characteristics are the I/Q signals, that is, a case where the I/Q beamforming is adopted, will be described as an example unless otherwise specified.

Subsequently, a specific configuration and functions of the receiving circuit provided in the T/R circuit 11 will be described with reference to FIGS. 4 to 12.

FIG. 4 is a block diagram showing a configuration of a receiving circuit provided in the T/R circuit 11.

FIG. 4 shows a receiving circuit 111 provided in the T/R circuit 11. The receiving circuit 111 includes an amplifier 51, an analog to digital (A/D) conversion circuit 52, a quadrature detection circuit 53, a delay control circuit 54, an addition circuit 55, a filter processing circuit 56, a frequency characteristic analysis circuit 57, and a filter setting circuit 58.

The amplifier 51 has a function of amplifying signals received from the ultrasonic probe 20 for each channel and performing a gain correction processing under the control of the processing circuitry 17. The amplifier 51 can improve the image quality of the ultrasonic image by controlling the gain.

The A/D conversion circuit 52 has a function of subjecting the gain-corrected reception signals, which is the output of the amplifier 51, to A/D conversion for each channel under the control of the processing circuitry 17.

The quadrature detection circuit 53 has a function of performing quadrature detection on RF signals that are reception signals and converting the RF signals into I/Q signals each including an "I" signal and a "Q" signal for each channel.

The delay control circuit 54 has a function of giving, for each channel, a delay time necessary for determining the reception directivity to the I/Q signals output from the A/D conversion circuit 52 under the control of the processing circuitry 17. The delay control circuit 54 can improve the image quality of the ultrasonic image by controlling the reception delay curve given to the I/Q signals.

The addition circuit 55 has a function of performing phase rotation and weighting control (apodization) for each channel on the I/Q signals output from the delay control circuit 54 to acquire the I/Q signals, thereby adding the acquired I/Q signals and generating beam data of the I/Q signals. By the addition processing of the addition circuit 55, a reflection component from a direction corresponding to the reception directivity of the reception signals is emphasized.

The filter processing circuit 56 has a function of applying an arbitrary complex reception filter to the I/Q signals output from the addition circuit 55 under the control of the processing circuitry 17, and a function of outputting the I/Q signals to which the complex reception filter has been applied to the B mode processing circuit 12 and the Doppler processing circuit 13. The filter processing circuit 56 is an example of a filter processor.

As described above, the image quality of the ultrasonic image can be improved to some extent by the gain control by the amplifier 51 and the control of the reception delay curve by the delay control circuit 54. However, since the ultrasonic attenuation changes for each individual and of each depth, it is difficult to optimize the image quality of the ultrasonic wave only by controlling those. Therefore, the receiving circuit 111 provided in the T/R circuit 11 includes the frequency characteristic analysis circuit 57 and the filter setting circuit 58.

The frequency characteristic analysis circuit 57 has a function of performing a frequency analysis on an I/Q signal in each region of interest according to the depth under the control of the processing circuitry 17 based on the I/Q signals output from the addition circuit 55, thereby acquiring a frequency characteristic. For example, the frequency characteristic analysis circuit 57 can perform frequency analysis by performing a fast Fourier transform (FFT) on the I/Q signal in each region of interest. The frequency characteristic analysis circuit 57 is an example of a frequency characteristic analyzer.

The filter setting circuit 58 sets, under the control of the processing circuitry 17, a complex reception filter in each region of interest, which is output from the frequency characteristic analysis circuit 57, such that the frequency characteristic of each region of interest shows a predetermined frequency characteristic. The filter coefficient of the complex reception filter is a complex coefficient including a real part and an imaginary part.

In the case of the I/Q beamforming, when the waveform of the I/Q signal in each region of interest slightly changes the frequency of the waveform of the RF signal, the modulated signal can be treated as a complex amplitude. The filter setting circuit 58 is an example of a filter setting unit.

Under the control of the processing circuitry 17, the filter processing circuit 56 includes a function of applying the complex reception filter of each region of interest output from the filter setting circuit 58 to the I/Q signals output from the addition circuit 55 such that feedback is performed, and a function of outputting the I/Q signals to which the complex reception filter has been applied to the B mode processing circuit 12 or the Doppler processing circuit 13 as baseband data, in addition to the function described above. That is, the filter processing circuit 56 applies the complex reception filter to a second I/Q signal after a first I/Q signal, which is the basis for setting the complex reception filter, in each region of interest, and converts the second I/Q signal into a third I/Q signal. Then, the image generating circuit 14 (shown in FIG. 1) generates the ultrasonic image in substantially real time based on the data based on the third I/Q signal from the B mode processing circuit 12 (or the Doppler processing circuit 13). It should be noted that "substantially real time" includes a case where an ultrasonic image is generated (or displayed) simultaneously with transmission of an ultrasonic wave. Further, "substantially real time" includes a case where there is a time lag from transmission of an ultrasonic wave to generation (or display) of an ultrasonic image for a processing time from transmission of an ultrasonic wave to generation (or display) of an ultrasonic image. Subsequently, an operation of the ultrasonic diagnostic apparatus 10 will be described.

Each of FIGS. 5 and 6 is a diagram showing the operation of the ultrasonic diagnostic apparatus 10 as a flowchart. In FIGS. 5 and 6, reference numerals with numbers attached to "ST" indicate respective steps in the flowchart. In FIGS. 5 and 6, the case of I/Q beamforming, that is, the case where the reception filter is a complex reception filter will be described as an example.

As shown in FIG. 5, the processing circuitry 17 of the ultrasonic diagnostic apparatus 10 controls the T/R circuit 11 and the like to start an ultrasonic scan using the ultrasonic probe 20 (step ST1).

The frequency characteristic analysis circuit 57 acquires I/Q signals for one frame, which are the output of the addition circuit 55 (step ST2). The frequency characteristic analysis circuit 57 performs the frequency analysis on an I/Q signal in the region of interest corresponding to the depth among the I/Q signals for one frame acquired in step ST2 to acquire frequency characteristics (step ST3).

The filter setting circuit 58 sets a complex reception filter for correcting the waveform of the frequency characteristic of the region of interest such that the frequency characteristic of the region of interest acquired in step ST3 shows a predetermined frequency characteristic. Specifically, it is based on steps ST4 to ST8 described later. The filter setting circuit 58 calculates the gravity center from the frequency characteristics of the region of interest acquired in step ST3 (step ST4).

The filter setting circuit 58 sets a target signal strength (step ST5). The filter setting circuit 58 sets a target frequency characteristic, based on the waveform of the frequency characteristic obtained in step ST3, the gravity center set in step ST4, the target signal strength set in step ST5, and the substantially flat bandwidth indicated by the designed frequency characteristic (step ST6). The designed frequency characteristics are those set in advance before the ultrasonic scan is started, or those optimized according to the acquired frequency characteristics.

For example, the filter setting circuit 58 acquires a waveform having a target signal strength near the position of the gravity center and having a substantially flat bandwidth close to a substantially flat bandwidth in design. The waveform is based on the waveform of the clinical frequency characteristic acquired in step ST3. For example, the waveform of the clinical frequency characteristic can be used as an envelope.

The filter setting circuit 58 sets a complex reception filter for the region of interest, and the complex reception filter shapes the waveform such that the frequency characteristic of the I/Q signal in the region of interest acquired in step ST3 indicates the target frequency characteristic set in step ST6 (step ST7), and stores the complex reception filter of the region of interest in the main memory 18 (step ST8). The operator may adjust the frequency characteristics of the set complex reception filter via the input interface 30 (adjustment switch).

Each of FIGS. 7A and 7B is a diagram showing a complex reception filter of the region of interest.

FIG. 7A shows a frequency characteristic of an I/Q signal in the region of interest, a target frequency characteristic of the region of interest, and a frequency characteristic of a complex reception filter of the region of interest. A complex reception filter for shaping the waveform is set for each region of interest such that the frequency characteristic of the I/Q signal in the region of interest indicates the target frequency characteristic.

In the case of I/Q beamforming, when the waveform of the I/Q signal in each region of interest slightly changes the frequency of the waveform of the RF signal, the modulated signal can be treated as a complex amplitude. The filter coefficient of the complex reception filter is a complex coefficient including a real part and an imaginary part.

Returning to the description of FIG. 5, the filter setting circuit 58 determines whether or not complex reception filters have been set at all depths, that is, in all regions of interest (step ST9). If it is determined as "NO" in step ST9, that is, if it is determined that the complex reception filters are not set in all the regions of interest, the frequency characteristic analysis circuit 57 shifts the depth of the region of interest (step ST10), and frequency-analyzes the shifted I/Q signal in the region of interest based on the I/Q signal for one frame acquired in step ST2 to acquire frequency characteristics (step ST3).

On the other hand, if it is determined as "YES" in step ST9, that is, if it is determined that the complex reception filters have been set in all the regions of interest, the processing proceeds to the steps in FIG. 6.

Each of FIGS. 8A and 8B is a diagram showing a complex reception filter of each region of interest. FIG. 8 shows a complex reception filter of each region of interest when divided into eight in the depth direction.

FIG. 8A shows the filter coefficients of the real part components in each region of interest, that is, at each depth. FIG. 8B shows the filter coefficient of the imaginary part component in each region of interest, that is, at each depth. As shown in FIGS. 8A and 8B, appropriate filter coefficients are calculated for the real part component and the imaginary part component of each region of interest.

Returning to the description of FIG. 6, the filter processing circuit 56 applies the complex reception filter in each region of interest registered in step ST8 to the I/Q signals of one frame output from the addition circuit 55 such that feedback is performed (step ST11).

FIG. 9 is a diagram showing, as a frequency characteristic, an effect acquired when a complex reception filter is applied to the I/Q signal in a predetermined region of interest.

FIG. 9 shows frequency characteristics before a complex reception filter is applied to I/Q signals for one frame. FIG. 9 also shows frequency characteristics after applying a complex reception filter to I/Q signal in a predetermined region of interest among I/Q signals for one frame. The complex reception filter in each region of interest registered in step ST8 is fed back and applied to the I/Q signals for one clinical frame, which is the output of the addition circuit 55. As a result, the frequency characteristics of the I/Q signals for one clinical frame are corrected to the target frequency characteristics, and a substantially flat bandwidth is expanded.

Returning to the description of FIG. 6, the B mode processing circuit 12 (or Doppler processing circuit 13) and the image generating circuit 14 generate an ultrasonic image for one frame based on the I/Q signals in the entire range to which the complex reception filter has been applied in step ST11 (step ST12).

Each of FIGS. 10A and 10B is a diagram showing an effect acquired when a complex reception filter is applied to the I/Q signal in a predetermined region of interest as an ultrasonic image (for example, a B mode image). The imaging target (part) of the B mode image shown in each of FIGS. 10A and 10B is a kidney.

FIG. 10A shows a B mode image before applying a complex reception filter to I/Q signals for one frame. FIG. 10B shows a B mode image after applying a complex reception filter to an I/Q signal in a predetermined region of interest, for example, a region of interest R, of I/Q signals for one frame.

The B mode imaging region shown in FIG. 10A is compared with the B mode imaging region shown in FIG. 10B. According to the B mode imaging region shown in FIG. 10B, the distance resolution of the structure in the region of interest R of the kidney is improved. As a result, the image quality is optimized, and it is possible to more clearly recognize the area of interest R.

Returning to the description of FIG. 6, the filter processing circuit 56 determines whether to finish the ultrasonic scan started in step ST1 (step ST13). For example, the filter processing circuit 56 determines whether or not to finish the ultrasonic scan by a finish operation by the operator via the input interface 30. If it is determined as "NO" in step ST13, that is, if it is determined that the ultrasonic scan started in step ST1 is not to be finished, the filter processing circuit 56 proceeds to the next frame (step ST14), and applies the coefficients of the complex reception filter registered in step ST8 to the I/Q signals of the next one frame such that feedback is performed (step ST11).

On the other hand, if it is determined as "'YES" in step ST13, that is, if it is determined that the ultrasonic scan started in step ST1 is to be finished, the processing circuit 17 of the ultrasonic diagnostic apparatus 10 controls the T/R circuit 11 and the like, thereby finishes the ultrasonic scan using the ultrasonic probe 20.

The case where, in the ultrasonic scan for the same patient and the same imaging part, the complex reception filter set and registered once is applied to I/Q signals of frames generated thereafter has been described with reference to FIGS. 5 and 6. In other words, the same complex reception filter is used during a series of ultrasonic examinations for scanning the same imaging part. However, it is not limited to that case. For example, the complex reception filter may be set every time in each frame, or may be set at fixed intervals. The necessity of setting the complex reception filter may be switched of each frame according to the movement of the ultrasonic probe 20.

In this case, the frequency characteristic analysis circuit 57 may first-determine whether or not the change in a values indicating the scan section is equal to or greater than a first threshold value. If the change in the value indicating the scan section is greater than or equal to the first threshold value, and a value indicating the scan section after the first-determining is less than a second threshold value (may be the same as the first threshold value), that is, the value has almost no change. Then, the frequency characteristic analysis circuit 57 performs the frequency analysis of the I/Q signals again, or return to the complex receive filter, which was originally set as a fixed value in the apparatus. The value indicating the scan section is a value indicating at least one of the position and the angle of the ultrasonic probe 20 corresponding to the scan section. Alternatively, the value indicating the scan section is a luminance value of an ultrasonic image corresponding to the scan section. The luminance value of the ultrasonic image means an average luminance value, a maximum luminance value, a minimum luminance value, or a variation in the luminance value in pixels included in the ultrasonic image (or the region of interest).

In other words, while the position and angle of the ultrasonic probe 20 change to some extent between the frames, the change in the value indicating the scan section is less than the first threshold value, thereby, resetting of the complex reception filter is not performed. Alternatively, while the average luminance value of pixels included in the ultrasonic image (or the region of interest) changes to some extent between frames, the change in the value indicating the scan section is less than the first threshold value, thereby, resetting of the complex reception filter is not performed. The change in the value indicating the scan section may be based on data acquired by an acceleration sensor (not shown) capable of measuring the angle of the ultrasonic probe 20 provided in the ultrasonic probe 20. The change in the value indicating the scan section may be based on data acquired by a magnetic sensor (not shown) capable of measuring the position and the angle of the ultrasonic probe 20 by generating a magnetic field. Alternatively, when a sensor is not used, the change in the value indicating the scan section may be detected from a temporal change in multiple image data.

Further, the complex reception filter set in the past and the value indicating the scan section (for example, the position of the ultrasonic probe 20) may be registered in the main memory 18. In this case, if it is determined that a scan section of the same position has been scanned in a series of ultrasonic examinations as the past, the filter processing circuit 56 acquires and uses a complex reception filter corresponding to the scan section from the main memory 18. Thereby, the load for setting the complex reception filter is reduced.

Alternatively, the frequency characteristic analysis circuit 57 may acquire a value indicating a scan section at regular time intervals. In this case, if the frequency characteristic analysis circuit 57 determines that the change in the value from the previous setting of the complex reception filter is equal to or greater than a third threshold value, the frequency characteristic analysis circuit 57 performs the frequency analysis on the I/Q signal again. That is, if the position or angle of the ultrasonic probe 20 in a certain flame changes to some extent from a frame before the regular time from the certain flame, the complex reception filter is reset. This is because the change in the value indicating the scan section is equal to or more than the third threshold value.

Alternatively, the frequency characteristic analysis circuit 57 determines whether or not the change in a value indicating a condition such as a depth of field (including a display target depth, a zoom, etc.) via the input interface 30 is equal to or greater than a fourth threshold value. When the frequency characteristic analysis circuit 57 determines that the change in the value indicating the condition is equal to or greater than the fourth threshold value, the frequency characteristic analysis circuit 57 performs the frequency analysis of the I/Q signals again, or resets the complex reception filter originally set to a fixed value in the apparatus. The depth of field defines the size of the image of an object. When the depth of field is set deep, the object is displayed in a relatively small image. On the other hand, if the depth of field is set to be shallow, the object is displayed as a relatively large image.

Designed frequency characteristics are distorted due to the amount of ultrasonic attenuation from the designed frequency band. However, according to the ultrasonic diagnostic apparatus 10, it is possible to correct instantaneously (or almost in real time) the distortion. As a result, it is possible to suppress image quality degradation due to ultrasonic attenuation, thereby provide a high-quality ultrasonic image.

2. First Modification

The filter setting circuit 58 is not limited to acquiring one target frequency characteristic from the frequency characteristics of the I/Q signal in each region of interest in order to set the reception filter. For example, the filter setting circuit 58 synthesizes multiple frequency components, that is, generates an ultrasonic image by frequency compounding. In this case, a complex reception filter is set for each frequency component set in each region of interest. The filter setting circuit 58 acquires a target frequency characteristic on the low frequency side and a target frequency characteristic on the high frequency side from the frequency characteristics of the I/Q signal in each region of interest.

In this case, the filter processing circuit 56 corrects the clinical frequency characteristic so as to show the frequency characteristic of each target. Then, the image generating circuit 14 synthesizes the ultrasonic images acquired with the frequency characteristics of each target. As a result, it is effective in improving the contrast resolution and improving the uniformity of the resulting image.

FIG. 11 is a diagram for explaining the frequency compound.

The upper part of FIG. 11 shows the target, that is, the target frequency characteristic (center frequency f1) on the low frequency side and the target frequency characteristic (center frequency f2) on the high frequency side in the region of interest at the depth of the imaging target. The lower part of FIG. 11 shows a target frequency characteristic on the low frequency side (center frequency f1) and a target frequency characteristic on the high frequency side (center frequency f2) in a deep region of interest where ultrasonic attenuation is large. When frequency compounding is performed, as shown in FIG. 11, it is preferable that the level, that is, the intensity is matched between the target frequency characteristic on the low frequency side and the target frequency characteristic on the high frequency side.

3. Second Modification

When performing the frequency analysis on the I/Q signal in each region of interest according to the depth, the frequency characteristic analysis circuit 57 may set each region of interest to include the center position in the scanning direction in the imaging region. This is because the desired area is often near the center of the imaging region. However, it is not limited to that case. For example, the frequency characteristic analysis circuit 57 can also set multiple regions of interest of the same depth and perform frequency analysis in a region of interest selected from the set multiple regions of interest.

FIG. 12 is a diagram showing a method of selecting a predetermined region of interest from the set multiple regions of interest of the same depth.

FIG. 12 simulates the imaging region of the B mode image. Multiple regions of interest are set of the same depth along the scanning direction (the horizontal direction in FIG. 12). Then, the frequency characteristic analysis circuit 57 performs noise determination on the multiple regions of interest of the same depth. The frequency characteristic analysis circuit 57 determines whether the S/N (Signal to Noise) is higher than a fifth threshold value for the multiple regions of interest of the same depth in order from the center position in the scanning direction to the outer position. For example, the frequency characteristic analysis circuit 57 performs noise determination in the region of interest at the center position in the scanning direction at the shallowest part of the imaging region. Thereafter, the frequency characteristic analysis circuit 57 determines that the region of interest is a signal region, and performs a frequency analysis in the region of interest.

Subsequently, the frequency characteristic analysis circuit 57 performs noise determination in the region of interest at the center position in the scanning direction in the second shallowest part of the imaging region. Thereafter, the frequency characteristic analysis circuit 57 determines that the region of interest is a noise region. Subsequently, in the second shallowest part of the imaging region, the frequency characteristic analysis circuit 57 performs a noise determination in the region of interest on the left of the center position. Thereafter, the frequency characteristic analysis circuit 57 determines that the region of interest is the signal region, and performs frequency analysis in the region of interest.

Subsequently, the frequency characteristic analysis circuit 57 performs a noise determination in the region of interest at the center position in the scanning direction in the third shallowest part of the imaging region. Thereafter, the frequency characteristic analysis circuit 57 determines that the region of interest is the noise region. Subsequently, the frequency characteristic analysis circuit 57 performs noise determination in the region of interest on the left of the center position in the third shallowest part of the imaging region. Thereafter, the frequency characteristic analysis circuit 57 determines that the region of interest is the noise region. Subsequently, the frequency characteristic analysis circuit 57 performs noise determination in the region of interest on the right of the center position in the third shallowest part of the imaging region. Thereafter, the frequency characteristic analysis circuit 57 determines that the region of interest is the signal region, and performs frequency analysis in the region of interest.

In the present embodiment, none of the regions of interest at a certain depth may be the signal region. In this case, a dynamic filter preset in the apparatus may be used, one reception filter set at one shallower or deeper depth may be used, or a representative value (for example, an average value) of two reception filters set at one shallower and deeper depth may be used is used as the reception filter of the depth.

When the multiple regions of interest are set along the scanning direction of the same depth, the filter setting circuit 58 may set different complex reception filters for the multiple regions of interest. In this case, the multiple regions of interest of the same depth along the scanning direction are multiple regions of interest divided into a grid on the raw data space before scan conversion. Then, the frequency analysis of the I/Q signal in each lattice is performed.

According to at least one embodiment described above, it is possible to suppress image quality degradation due to ultrasonic attenuation, thereby provide a high-quality ultrasonic image.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus, comprising:
   a frequency characteristic analysis circuit configured to perform a frequency analysis on a first reception signal corresponding to a region of interest of each depth, of multiple depths, among reception signals of ultrasonic waves, and acquire a frequency characteristic of each depth;
   a filter setting circuit configured to set a reception filter of each depth based on the acquired frequency characteristic of each depth such that a signal of each depth resulting from application of the reception filter has a predetermined frequency characteristic;
   a filter processing circuit configured to apply the set reception filter of each depth to a second reception signal corresponding to the region of interest of each depth among the reception signals, the second reception signal being after the first reception signal, and convert the second reception signal into a third reception signal corresponding to the region of interest of each depth among the reception signals; and
   an image generating circuit configured to generate an ultrasonic image in substantially real time based on the converted third reception signal corresponding to the region of interest of each depth of the multiple depths, wherein
   the frequency characteristic analysis circuit is further configured to set, prior to the frequency analysis of the reception signals in the region of interest of each depth being performed, the region of interest within an imaging region of the ultrasonic image to include a center of the imaging region in a scanning direction.

2. The ultrasonic diagnostic apparatus according to claim 1, wherein the filter setting circuit is further configured to set, when generating an ultrasonic image by combining multiple frequency components in the region of interest of each depth, the reception filter of each depth for the multiple frequency components set in the region of interest of each depth.

3. The ultrasonic diagnostic apparatus according to claim 1, wherein the frequency characteristic analysis circuit is further configured to:
   set multiple regions of interest of a same depth, and
   perform the frequency analysis in a particular region of interest selected from the set multiple regions of interest.

4. The ultrasonic diagnostic apparatus according to claim 3, wherein the frequency characteristic analysis circuit is further configured to perform the frequency analysis in the particular region of interest, which has a higher S/N (Signal to Noise) than a threshold value among the set multiple regions of interest of same depth.

5. The ultrasonic diagnostic apparatus according to claim 1, wherein each of the reception signals is an I (In-phase)/Q (Quadrature-phase) signal, and a filter coefficient of the reception filter is a complex coefficient.

6. The ultrasonic diagnostic apparatus according to claim 1, wherein the filter setting circuit is further configured to set the reception filter of each depth such that the signal of each depth resulting from the application of the reception filter is substantially flat in a wide band.

7. The ultrasonic diagnostic apparatus according to claim 6, wherein the filter setting circuit is further configured to set the reception filter of each depth such that the signal of each depth resulting from the application of the reception filter is symmetrical on a low frequency side and a high frequency side with respect to a center frequency.

8. The ultrasonic diagnostic apparatus according to claim 1, further comprising:
an adjustment switch configured to adjust a frequency characteristic of the set reception filter.

9. The ultrasonic diagnostic apparatus according to claim 1, wherein the frequency characteristic analysis circuit is further configured to:
determine that a change in a value indicating a scan section is equal to or greater than a first threshold value, the scan section being a cross-section in which the ultrasonic waves are transmitted and received,
after the determination, determine that the change in the value indicating the scan section is less than a second threshold value, and
perform the frequency analysis on a fourth reception signal corresponding to the region of interest of each depth, the fourth reception signal being received after the first reception signal, thereby setting the reception filter at an interval of frames, and not every frame.

10. The ultrasonic diagnostic apparatus according to claim 1, wherein the frequency characteristic analysis circuit is further configured to:
acquire values indicating a scan section at a regular time interval, the scan section being a cross-section in which the ultrasonic waves are transmitted and received,
determine that a change from a first value of the values at the previous set reception filter before the regular time interval to a second value of the values after the regular time interval is equal to or greater than a threshold value, and
perform the frequency analysis on a fourth reception signal corresponding to the region of interest of each depth, the fourth reception signal being received after the first reception signal.

11. The ultrasonic diagnostic apparatus according to claim 1, wherein the frequency characteristic analysis circuit is further configured to:
determine that a change in a value indicating a condition of a depth of field is equal to or greater than a threshold value, and
perform the frequency analysis on a fourth reception signal corresponding to the region of interest of each depth, the fourth reception signal being received after the first reception signal.

12. The ultrasonic diagnostic apparatus according to claim 1, wherein the filter processing circuit is further configured to acquire and use, when a scan section for a same position as in a past has been scanned in a series of ultrasonic examinations of scanning while changing the scan section, a reception filter corresponding to the scan section, the scan section being a cross-section in which the ultrasonic waves are transmitted and received.

13. An ultrasonic diagnostic apparatus, comprising:
a frequency characteristic analysis circuit configured to perform a frequency analysis on a first reception signal corresponding to a region of interest of each depth, of multiple depths, among reception signals of ultrasonic waves, and acquire a frequency characteristic of each depth;
a filter setting circuit configured to set a reception filter of each depth based on the acquired frequency characteristic of each depth such that a signal resulting from application of the reception filter has a predetermined frequency characteristic;
a filter processing circuit configured to apply the set reception filter of each depth to a second reception signal corresponding to the region of interest of each depth among the reception signals, the second reception signal being after the first reception signal, and convert the second reception signal into a third reception signal corresponding to the region of interest of each depth among the reception signals; and
an image generating circuit configured to generate an ultrasonic image based on the converted third reception signal corresponding to the region of interest of each depth of the multiple depths, wherein
the frequency characteristic analysis circuit is further configured to
set, prior to the frequency analysis of the reception signals in the region of interest of each depth being performed, the region of interest within an imaging region of the ultrasonic image to include a center of the imaging region in a scanning direction,
determine that a change in a value indicating a scan section is equal to or greater than a first threshold value, the scan section being a cross-section in which the ultrasonic waves are transmitted and received,
after the determination, determine that the change in the value indicating the scan section is less than a second threshold value, and
perform the frequency analysis on a fourth reception signal corresponding to the region of interest of each depth, the fourth reception signal being received after the first reception signal.

14. The ultrasonic diagnostic apparatus according to claim 13, wherein the value indicating the scan section is a value indicating a position or an angle of an ultrasonic probe corresponding to the scan section.

15. The ultrasonic diagnostic apparatus according to claim 13, wherein the value indicating the scan section is a luminance value of an ultrasonic image corresponding to the scan section.

16. The ultrasonic diagnostic apparatus according to claim 13, wherein the filter processing circuit is further configured to acquire and use, when the scan section for a same position as in a past has been scanned in a series of ultrasonic examinations of scanning while changing the scan section, a reception filter corresponding to the scan section.

17. An ultrasonic diagnostic apparatus, comprising:
a frequency characteristic analysis circuit configured to perform a frequency analysis on a first reception signal corresponding to a region of interest of each depth, of multiple depths, among reception signals of ultrasonic waves, and acquire a frequency characteristic of each depth;
a filter setting circuit configured to set a reception filter of each depth based on the acquired frequency characteristic of each depth such that a signal of each depth resulting from application of the reception filter has a predetermined frequency characteristic;
a filter processing circuit configured to apply the set reception filter of each depth to a second reception signal corresponding to the region of interest of each depth among the reception signals, the second reception signal being after the first reception signal, and convert the second reception signal into a third reception signal corresponding to the region of interest of each depth among the reception signals; and
an image generating circuit configured to generate an ultrasonic image based on the converted third reception signal corresponding to the region of interest of each depth of the multiple depths, wherein the frequency characteristic analysis circuit is further configured to set, prior to the frequency analysis of the reception signals in the region of interest of each depth being performed, the region of interest within an imaging region of the ultrasonic image to include a center of the imaging region in a scanning direction, determine that change in a value indicating a condition of a depth of field is equal to or greater than a threshold value, and perform the frequency analysis on a fourth reception signal corresponding to the region of interest of each depth, the fourth reception signal being received after the first reception signal.

* * * * *